United States Patent [19]

Dickerman et al.

[11] Patent Number: 5,113,857
[45] Date of Patent: May 19, 1992

[54] BREATHING GAS DELIVERY SYSTEM AND HOLDING CLIP MEMBER THEREFOR

[76] Inventors: Stair Dickerman; JoAnn A. Dickerman, both of 10065 NE. Roberts Rd., Bainbridge Island, Wash. 98110

[21] Appl. No.: 572,395
[22] Filed: Aug. 27, 1990
[51] Int. Cl.⁵ ............................................. A61M 15/08
[52] U.S. Cl. ........................ 128/207.18; 128/206.11
[58] Field of Search ...................... 128/204.12, 206.11, 128/207.18, DIG. 26; 24/489, 543

[56] References Cited

U.S. PATENT DOCUMENTS

| | | | |
|---|---|---|---|
| 77,540 | 5/1868 | Seaver | 24/489 |
| 701,538 | 6/1902 | Carence | 128/204.12 |
| 2,526,586 | 10/1950 | Shuff | 128/204.12 |
| 2,672,138 | 3/1954 | Carlock | 128/207.18 |
| 3,747,597 | 7/1973 | Olivera | 128/206.11 |
| 3,902,486 | 9/1975 | Guichard | 128/206.11 |
| 4,699,139 | 10/1987 | Marshall et al. | 128/207.18 |
| 4,753,233 | 6/1988 | Grimes | 128/207.18 |
| 4,782,832 | 11/1988 | Trimble et al. | 128/207.18 |
| 4,915,105 | 4/1990 | Lee | 128/206.11 |

Primary Examiner—Edgar S. Burr
Assistant Examiner—Stephen R. Funk
Attorney, Agent, or Firm—George M. Cole

[57] ABSTRACT

A breathing gas air delivery device (10) for attachment to the calumella of the wearer's nose septum having a frame (12) which includes a U-shaped clip (14) with legs (16) and nasal septal engaging projections (18) which clip (14) in turn is connected to an outwardly spaced side frame piece (24,26) on each side of clip (14) and supported at least in part by a cross frame support piece (28,30) so that finger pressure on the side frame pieces (24,26) spreads the clip legs (16) and projections (18) for attachment and removal of the device. A pair of air intake tubes (32,34) are supported in the frame and are connected to filter holder menas (20,22). The filter holder means (20,22) may be attached to and supported on the frame or connected by tubular means (142, 146,148) to the air intake tubes. Sealant pads (36,38) block off the nasal openings except for air entering the nasal passages through said air intake tubes (32,34).

8 Claims, 6 Drawing Sheets

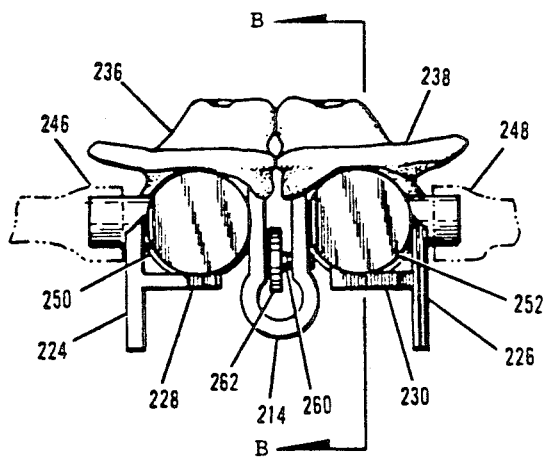
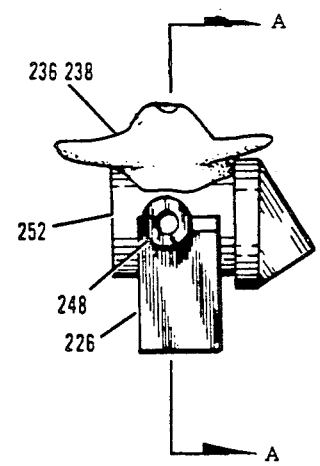
Figure 3A
Figure 3C
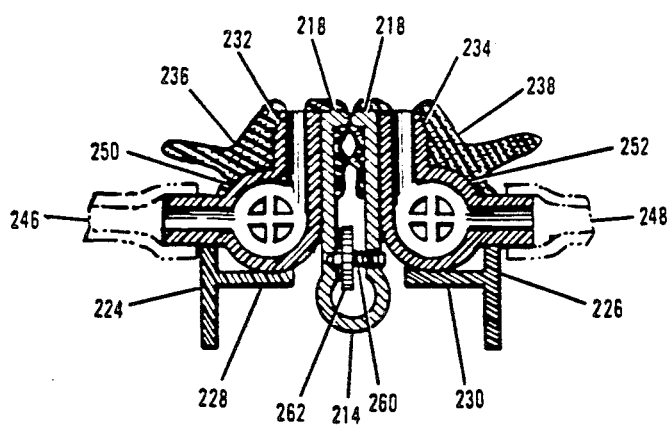
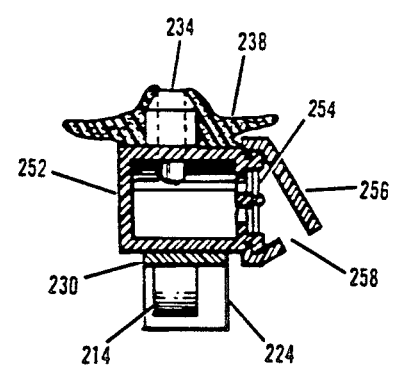
Figure 3B
Figure 3D

BREATHING GAS DELIVERY SYSTEM AND HOLDING CLIP MEMBER THEREFOR

TECHNICAL FIELD

The invention relates to the field of breathing gas delivery systems including filters for air to be breathed by human beings and to a holding clip means and more particularly does the invention relate to devices through which breathing gas and air are directed to the nasal passages and breathed and which devices include a holding clip member which attaches directly to the calumella of the wearer's nasal septum.

BACKGROUND ART

As those skilled in the art are aware in this age of health and safety consciousness, air filter devices intended for breathing by human beings which are readily available in the market place all have as their ultimate function removal of impurities, contaminates and other foreign matter from air entering human lungs. However, regardless of the design of air filter used, there are disadvantages which associate with each type.

One very common filter is the simple mask type dust filter having an elastic head band holding the mask over the mouth and nose. While they are simple and inexpensive they are also awkward, uncomfortable and hot. Such filters muffle the wearer's speech and require the user to remove the mask in order to eat, drink, clear the throat, blow one's nose or expectorate. In short they are a nuisance.

Another type of air filter is the more sophisticated and complicated canister device which is even more of a nuisance because it is heavier, more awkward and frequently covers more of the face and head. It is also more expensive and much more inconvenient to take off and put on. Many employees in lines of work in which the air is dirty and hazardous will still refuse to wear filters in spite of the danger to lungs and throat. In some situations individuals whose occupation subjects them to air contaminated with particles from grinding machines, sanding equipment, or asbestos, or workers who are exposed to chemical pollutants such as welding fumes, some floor finishes, or factory painting rooms, for example, are required to wear cumbersome respirators with large filter canisters. Again, the primary objections are the extreme discomfort and inconvenience associated with many of the commercially available devices.

Among the known prior art are the following United States Patents.

U.S. Pat. No. 3,457,917 shows a nasal filtering device which is designed to the shape of a nasal passage and which is individually insertable in the passage.

U.S. Pat. No. 2,663,297 is a surgical appliance for oxygen inhalation but which also includes a cannula. This device is not concerned with filtering.

U.S. Pat. No. 2,620,793 is a nose clip to block off and prevent water from passing through the nasal passages and causing pain, infection or inflammation to the wearer. This device is also not concerned with filtering.

U.S. Pat. No. 2,526,586 to Shuff is a device directed to a filter which is insertable in a wearer's nasal passage. This device provides for application of medication which is inserted in a nostril while it continues to serve as a filter. Attention, however, is directed to the clip 10 which has a pair of projections 18 adapted to embrace a suitable portion of the nose. The clip of this patent is structurally distinct and different from the clip member of this invention.

U.S. Pat. No. 2,426,161 is a device for filtering air which is worn inside each nostril but which nasal elements are connected to each other to prevent dislodgement.

U.S. Pat. No. 2,277,390 is a nasal inhaler device having two tubular members for nasal insertion and which are connected by a U-shaped element. Again, the device is worn internally of the nasal passage.

U.S. Pat. No. 2,264,153 is an insertable filter device in the form of two cage-like thimbles to be worn in the nasal passages. A U-shaped Yoke interconnects the two filter elements.

U.S. Pat. No. 2,219,801 is a medication holding device which is worn entirely internally of the nasal passage but which also functions as a filter. The structure can be adjusted to nostrils of different sizes.

U.S. Pat. No. 701,538 is a shield device which is simply a structural variation of the partially insertable filter elements interconnected by a bridge member outside the nose. The filter is intended to remove foreign matter such as pollen from air inhaled by the wearer.

None of the above patents teaches the structural and functional principles of applicant's device beyond the broad purpose of filtering air being breathed into the lungs. As such they are the most pertinent art known by applicant but still considered to be of interest only and not anticipatory of the invention disclosed and claimed herein.

DISCLOSURES OF THE INVENTION

The invention relates to a nose attached air filter or inhaler which comprises a small, light frame for holding the filter inhaler elements for each nostril, which elements are not insertable in the nasal passages. The device uses a U-shaped clip to attach to the relatively insensitive calumella of the nose just below the septal cartridge to hold the filter device against the nasal openings. The device is designed so that the wearer inhales through the nose and exhales through the mouth. In another embodiment, the filtering element or other air source may be larger and hence worn on the belt, for example, and the incoming air conveyed to the device by tube. In another embodiment exhalation can be through either the nose or mouth by incorporation of a check valve within the structure of the device.

Accordingly, it is among the many features of the invention to provide a device which delivers air and/or mixed breathing gases from a source such as a bottle or container as well as from a filter and which is designed for wearer convenience and comfort as well as for health and safety reasons. The device is light and small so that the wearer can attach it to the calumella and still not block or cover the mouth to prevent speaking or eating. It attaches quickly and conveniently and is small enough to fit under a welding visor. It frees the wearer of using a heavy sweaty device which covers most of the face and will not fog glasses or goggles.

BRIEF DESCRIPTION THE DRAWINGS

Figure 2:
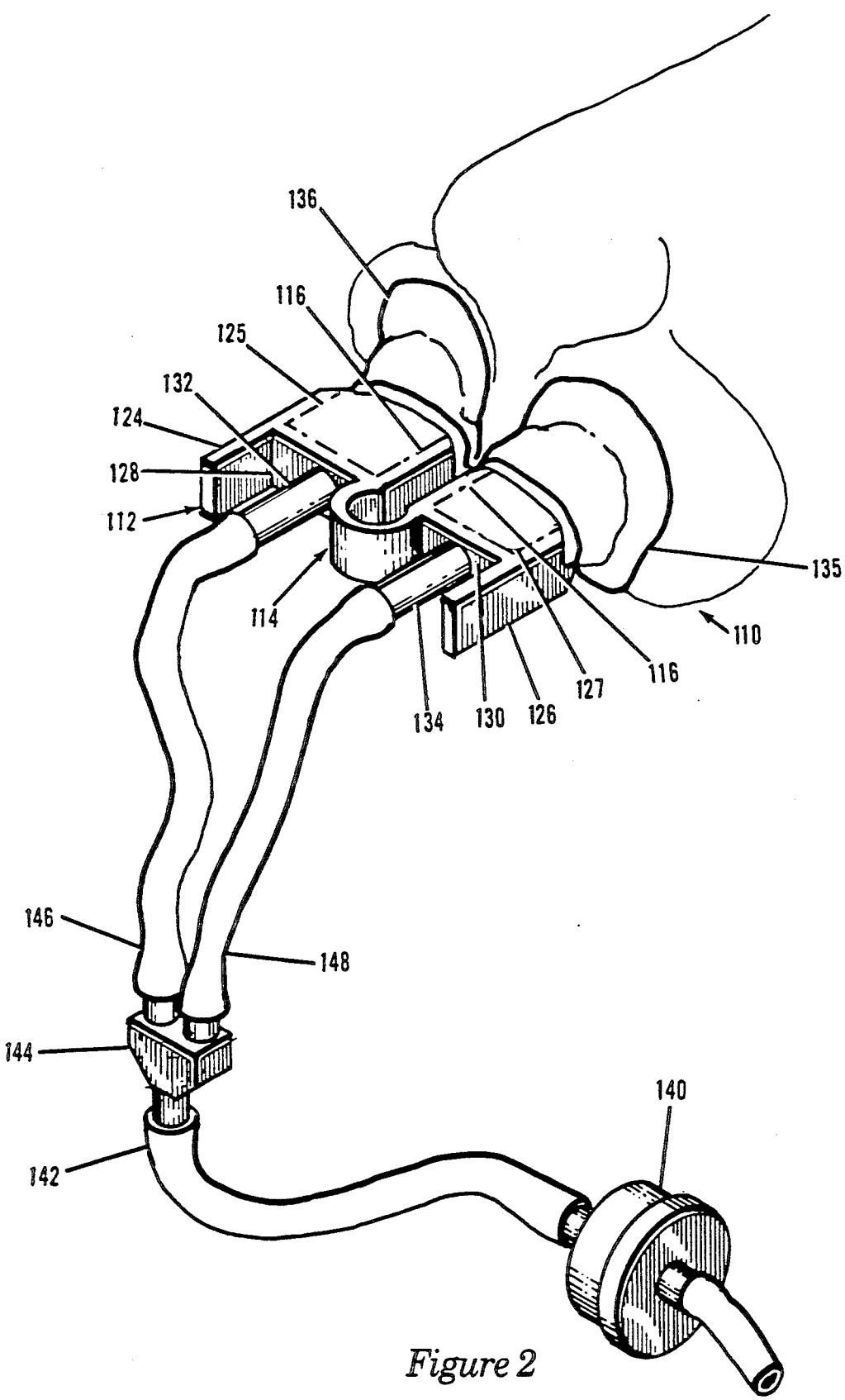
FIG. 2 is a perspective view of another embodiment of the device in which the filter portion is located away from the part attached to the nose.
Figure 2A:
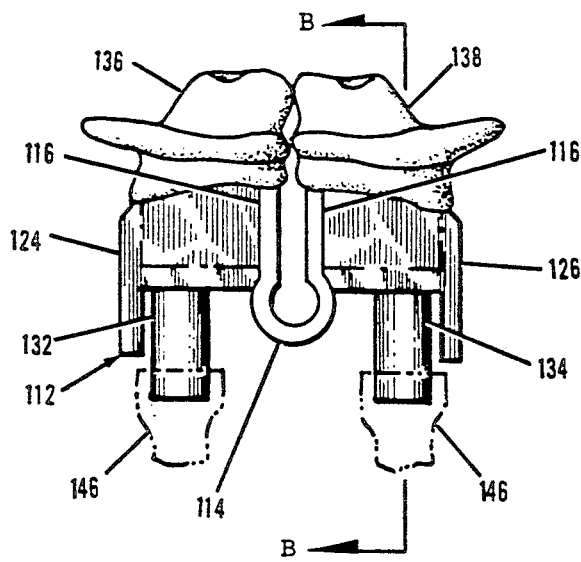
FIG. 2A is plan view of the device of FIG. 2 showing added details of construction.
Figure 2C:
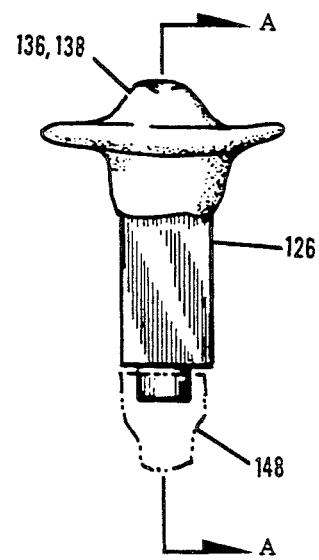
FIG. 2C is a side elevation view of the device to show more detail.
Figure 2B:
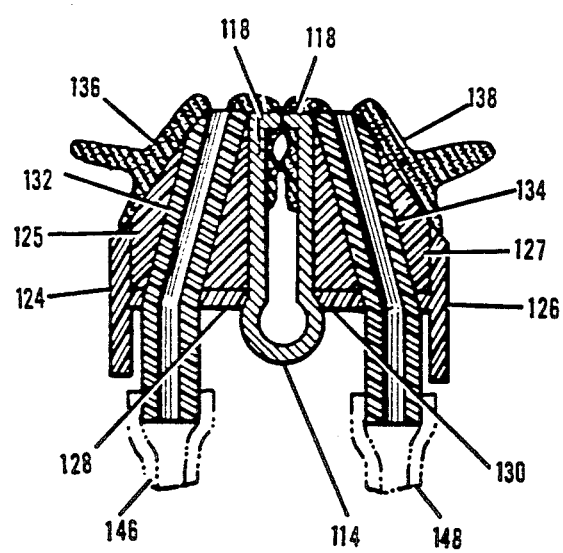
FIG. 2B is a cross section view along the line A—A of FIG. 2C.
Figure 3:
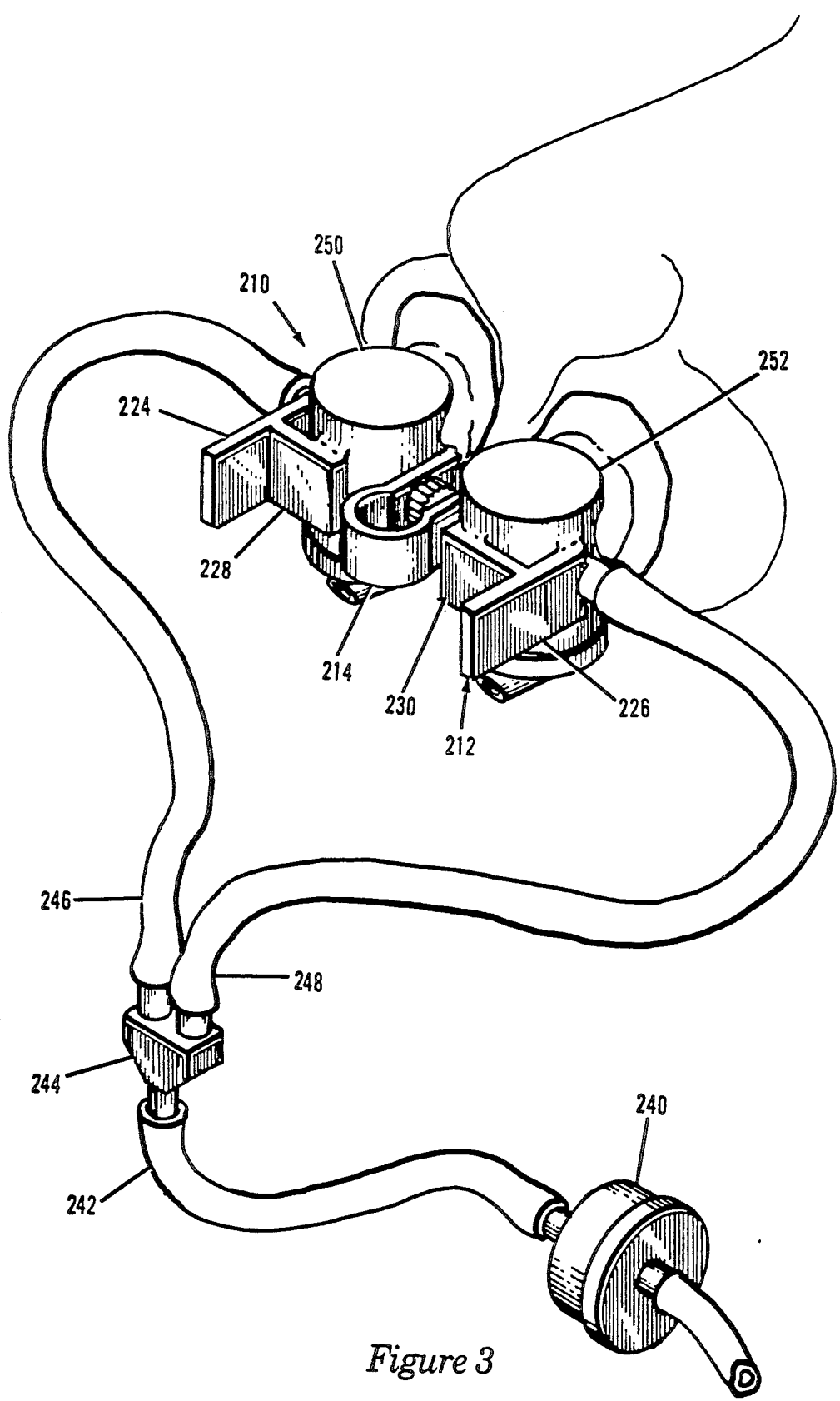

2D is a cross section view along the line B—B of FIG. 2A;

FIG. 3 is a perspective view of another embodiment of the device;

FIG. 3A is a top plan view of the embodiment of FIG. 3;

FIG. 3B is a cross section view taken along the line A—A of FIG. 3C showing details of construction;

FIG. 3C is a side elevation view showing details of construction; and

FIG. 3D is a cross section view taken along the line B—B of FIG. 3A showing additional details of construction.

BEST MODE FOR CARRYING OUT THE INVENTION

Figure 1:
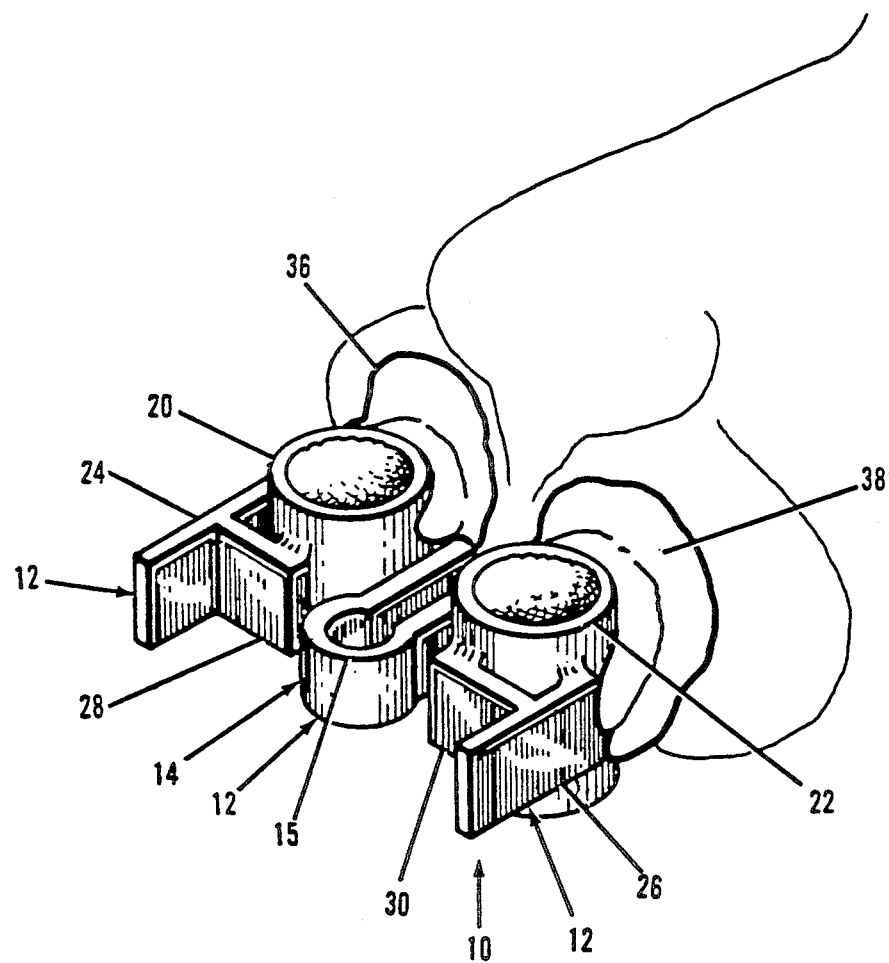
FIG. 1 shows a view in perspective of the device attached to the calumella portion of the septum in the nose.
Figure 1A:
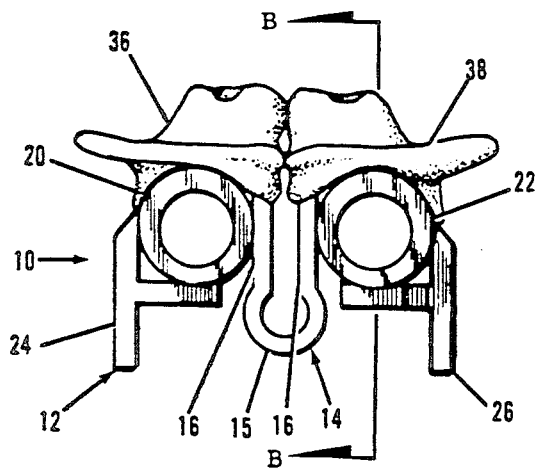
FIG. 1A is a top plan view of the device of FIG. 1 showing additional details of construction.
Figure 1C:
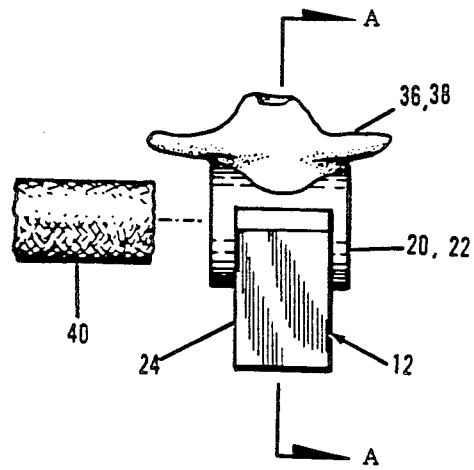
FIG. 1C is a side view of the device showing the filter cartridge removed.
Figure 1B:
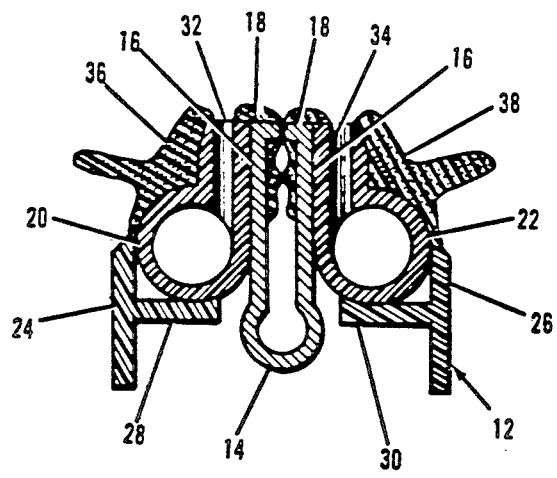
FIG. 1B is a cross section view of the device taken along the line A—A of FIG. 1C.
Figure 1D:
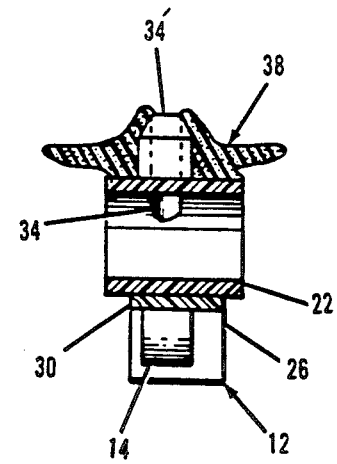
FIG. 1D is a cross section view taken along the line B—B of FIG. 1A.

Referring now to the drawings it will be seen in FIGS. 1-1D that the basic form of the invention is shown. The device, generally designated by the number 10, has a frame 12 which includes U-shaped clip member generally designated by the number 14 rounded at its base as at 15 with side pieces or legs 16. The legs 16 include rounded interior projections 18 at the open end for engaging the calumella immediately below the septal cartilage. It will be appreciated that the legs 16 of the clip are spring biased toward one another so that projections 18 engage the calumella with enough pressure to engage and hold to the calumella tissue but without causing the wearer any discomfort. The calumella is relatively insensitive so that a slight squeezing pressure exerted by the legs 16 on the engaging projections 18 does not cause the wearer any distress or pain.

Frame 12 includes a pair of cylindrical filter holders 20 and 22 attached to the legs 16 of clip 14 so that they are separated by the width of the clip. Attached to the outside of the holders 20 and 22 are side frame pieces 24 and 26 which extend from the holders outwardly a predetermined distance generally parallel to each other. Extending inwardly at right angles to the side frame pieces and attached both to the side frame pieces and to cylindrical filter holders 20 and 22 are short support cross frame pieces 28 and 30. Thus, it will be understood that a slight finger pressure on the outer ends of side frame pieces 24 and 26 will separate the projections 18 for removing or attaching the device to the calumella.

FIG. 1B shows connector passage 32 and 34 which interconnect from the filter holders to the nasal passages of the wearer. Also the area of the device around the holders and connector passages is provided with a soft, resilient sealant material in the form of pads 36 and 38 which block off the nasal opening so that when the wearer inhales through the nose air enters only through the device and not through the sealant pads.

Finally the replaceable filter and/or inhalent dispensing cartridge 40 is received in each of the two filter holders 20 and 22. The filter cartridges 40 are easily and quickly removed and replaced as they become clogged or exhausted.

Figure 2D:
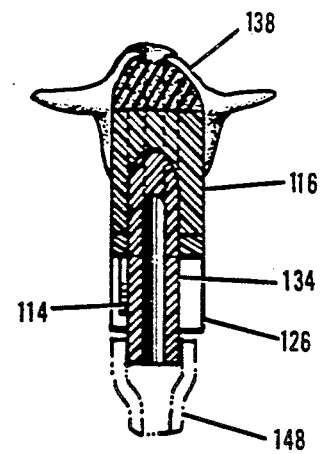

The embodiment of FIGS. 2-2D shows an embodiment which enables the use of a larger and therefore a longer lasting filter element before it must be replaced.

The device 110 has frame 112 with clip member 114 having legs 116 at the open end of which are smooth, rounded calumella engaging projections 118. Frame 112 has side frame pieces 124 and 126 and cross frame pieces 128 and 130 which attach to and interconnect clip 114 and side frame pieces 124 and 126. Top frame parts 125 and 127 and bottom frame parts 129 and 131 combine with other elements of frame 112 to define box structure through which the air intake tubes 132 and 134 extend. A check valve 140 which is optional is connected by tube 142 to a divider adapter or bifurcator 144. The adapter 144 separates into flexible tubes 146 and 148 which extend to air intake tubes 132 and 134 which in turn extend through cross frame pieces 128 and 130 and the box structure to the same depth as the inner ends of legs 116 when they open through pads 136 and 138 into the nasal openings. Again, this embodiment places the check valve 140 away from the frame itself such as, for instance, on a shoulder, on the belt of the wearer or in a filter holder.

The drawing views of FIGS. 3-3D show a slightly altered version of the embodiment of FIGS. 2-2D. The frame 212 includes side frame pieces 224 and 226 with inwardly extending cross frame pieces 228 and 230. A check valve 240 is connected by tube 242 to adapter 244 for separation into flexible tubes 246 and 248. This embodiment is provided with cylindrical valve housings 250 and 252 to which incoming tubes 246 and 248 connect. The cylindrical housings include air lines 232 and 234 extending to the nasal openings from the housings. At one end of the housings 250 and 252 it will be seen that there is a simple check valve 254 and outlet deflector 256 having an exhale opening 258. Thus, the wearer of this device takes in air via the filter and through the valve housings in which the check valve is closed. On exhale the expelled air exits out the valve housings through the check valves and thence to the openings 258.

An adjustment screw 260 and screw turning wheel 262 may be provided to regulate spring tension in the clip 214 in order to set pressure on the calumella at a desired level. Such tension adjustment may be included in the embodiments of 1-1D and 2-2D if desired. It will be appreciated that in the embodiments of 2-2D and 3-3D breathing gases in the tubes could be preheated or cooled for comfort and control of body temperature, as for instance, warming the incoming air in the tubes by laying the tube against the body. It is to be understood that all references to air herein pertain to both natural air, suitable mixtures of breathing gases and medical vapors which may be contained in bottles, cartridges, canisters or the like.

We claim:

1. Breathing gas delivery device for gas and air to be breathed by the wearer and for attachment to the nose septum of the wearer, comprising:

a) a frame means including a generally U-shaped clip portion which includes a base and a pair of legs having outer ends and inside surfaces which legs are spring biased toward each other and at said outer end of which legs on said inside surfaces thereof are projection means for engaging the calumella of the wearer's nose septum. said frame means also having a pair of side frame pieces each of which is spaced outwardly of said clip and which are generally parallel to each other and to said pair of legs. said side frame pieces and said legs being interconnected at least in part by cross support frame pieces. said side frame pieces extending away from the wearer's nose so that finger pressure applied on said side frame pieces squeezes said side frame pieces towards each other which thereby separates said legs and said projection means for attachment and removal of the device from the calumella, b) a pair of spaced apart air intake tubes supported in said frame with one each of said air intake tubes leading to a nasal opening.

b) sealant pad means for each nostril opening attached to said frame means such that an air intake tube for each nostril extends through said sealant pad means whereby said sealant pad means closes the nasal passage opening and permits inhaled air to pass into said air intake tubes and thence into the wearer's nose. and d) filter holder means connected to said frame means and to said air intake tubes and having air filter material or inhalent cartridge means therein for filtering air breathed in and passing in therethrough into said air intake tubes.

2. The breathing gas delivery device according to claim 1 and wherein said filter holder means includes two holders one each of which is located on said frame means on each side of said clip and is attached to said clip, to a cross support frame piece and to a side frame piece.

3. The breathing gas delivery device according to claim 2 and wherein said filter holders are cylindrical and open at least at one end thereof so that said filter material or inhalent cartridge can be installed and removed.

4. The breathing gas delivery device according to claim 3 and wherein one each of said air intake tubes is directly connected to and leads from a filter holder or other air source.

5. The breathing gas delivery device according to claim 1 and wherein said filter holder is located away from said frame means and connected by tubular means to said air intake tubes.

6. The breathing gas delivery device according to claim 5 and wherein said filter holder is connected by a single tubular member to an adapter device for separating the incoming air from said filter holder into two separate tubes one each of which is connected to an air intake tube on said frame.

7. The breathing gas delivery device according to claim 6 and wherein said frame includes a pair of check valve means one each of which is connected to said one of said two separate tubes and one each of which is connected to one of said air intake tubes on said frame so that the wearer can breathe in and out through the nose.

8. The breathing gas delivery device according to claim 7 and wherein said clip portion is provided with adjustment means for regulating the amount of spring pressure bearing on said legs and said projections of said clip portion.

* * * * *